United States Patent [19]
Gault

[11] 4,002,732
[45] * Jan. 11, 1977

[54] SPECKLE PARTICLE FOR DENTIFRICE

[75] Inventor: Ian Ray Gault, Lymm, England

[73] Assignee: Colgate-Palmolive Company, New York, N.Y.

[ * ] Notice: The portion of the term of this patent subsequent to Nov. 11, 1992, has been disclaimed.

[22] Filed: Sept. 15, 1975

[21] Appl. No.: 612,878

Related U.S. Application Data

[62] Division of Ser. No. 385,296, Aug. 3, 1973, Pat. No. 3,928,555.

[52] U.S. Cl. ............................................. 424/49
[51] Int. Cl.$^2$ ................................... A61K 7/16
[58] Field of Search ........................... 424/49–58

[56] References Cited

UNITED STATES PATENTS

| | | |
|---|---|---|
| 2,793,979 | 5/1957 | Svedres ............................ 424/22 |
| 2,805,977 | 9/1957 | Robinson et al. ............... 424/38 X |
| 2,875,130 | 2/1959 | Grass et al. ..................... 424/38 X |
| 3,146,167 | 8/1964 | Lantz et al. ...................... 424/22 |
| 3,279,998 | 10/1966 | Raff et al. ....................... 424/22 |
| 3,919,409 | 11/1975 | Perla et al. ...................... 424/52 |
| 3,928,555 | 12/1975 | Gault ................................ 424/22 |
| 3,928,559 | 12/1975 | Patino et al. .................... 424/49 |
| 3,934,001 | 1/1976 | Watson ............................ 424/49 |

OTHER PUBLICATIONS

Schmidt; H., Chem. Abstr., 75 No. 18443e (1971) of Devt. Stomatol., 19(10):800–810(1969), "Effectiveness of Dentrifrices and Special Additives from the Viewpoint of Periodontal Prophylaxis", (Allantoin in Dentrifrice).
Leigh, Chem. Abstr. 73, No. 7265F (1970) of Brit., 1,185,173, Mar. 25, 1970.
Ghilaroi, Chem. Abstr., 74, No. 141790x (1971) of Fr., 1,590,117, May 22, 1970.

*Primary Examiner*—Shep K. Rose
*Attorney, Agent, or Firm*—Robert L. Stone; Murray M. Grill; Herbert S. Sylvester

[57] ABSTRACT

Functional speckle particle suitable for use in dentifrice containing allantoin, aluminum dihydroxy allantoinate (ALDA) or aluminum chlorohydroxyallantoinate (ALCA). The speckle is effective in promoting healing of inflamed and bleeding gums or periodontal tissue.

9 Claims, No Drawings

SPECKLE PARTICLE FOR DENTIFRICE

This is a divisional of application Ser. No. 385,296, filed Aug. 3, 1973, now U.S. Pat. No. 3,928,555, patented Dec. 23, 1975.

This invention relates to novel particulate materials, to dentifrice compositions containing same and to the method of preparing said materials and compositions.

Uniformly colored as well as speckled dentifrices are known with the latter being of particular aesthetic appeal. In addition to non functional speckles, functional speckles, particularly of dental polishing agents are also known.

The present invention is directed to the provision of unique and novel speckles which are admirably suited for use in dentifrices, such as tooth powders and toothpastes. The speckles possess a desirable, functional character and are effective in promoting healing of inflamed and bleeding gums or periodontal tissue.

It is common for the gums or periodontal tissue of many individuals to become inflamed. When this occurs the gums are quite sensitive and bleed easily. Individuals having such periodontal conditions often find it difficult to provide adequate hygenic care to their teeth and gums due to the great pain they experience when they attempt to brush teeth and gums with a toothbrush and dentifrice composition.

Allantoin ($C_4H_6N_4O_3$) and aluminum dihydroxy allantoinate ($Al(OH)_2C_4H_5N_4O_3$), hereinafter referred to as ALDA, have been disclosed for use in dentifrice vehicles in view of their ability to combat sensitive periodontal tissue and promote its healing. Aluminum chlorohydroxy-allantoinate $Al_2(OH)_4ClC_4H_5N_4O_3$ hereinafter referred to as ALCA, possesses similar properties.

In recent years, visible speckles have been prepared which can be incorporated into dentifrices to provide desirable esthetic and visible effects. Some of the speckles also include functional components such as polishing agents, so that the user can better appreciate the hygenic effect provided by particular ingredients.

The provision of a functional dentifrice speckle which relieves the pain and sensitivity of periodontal conditions is highly desirable. Individuals having such conditions can actually "see" and perhaps "feel" the curative ingredient and therefore should be more apt to provide themselves with proper hygenic care when using dentifrices containing the ingredient.

It is an advantage of this invention that functional speckles are provided which contain an ingredient which alleviates periodontal sensitivity and bleeding.

It is a further advantage of this invention that a dentifrice is provided containing such speckles.

Other advantages of the invention will be apparent from the following description.

In accordance with certain of its aspects, this invention provides finely divided functional speckle particles comprising a matrix of metable binding material and about 5 – 10% by weight of an anti-irritant compound selected from the group consisting of allantoin, ALDA, and ALCA, said meltable binding material having a melting or softening point lower than the decomposition or melting point of said anti-irritant compound.

Allantoin is slightly-soluble in water (0.5% at 25°C) and has the empirical formula $C_4H_6N_4O_3$. In saturated aqueous solution it has a pH of about 4 – 6. It is effective in cleansing, healing and soothing, without irritation or sensitization, spongy or bleeding gums or periodontal tissue. Further, it aids in removing undesirable necrotic tissue and promotes the growth of cells of new and healthy tissue. Allantoin melts with decomposition at about 227°– 231°C.

ALDA, which has the empirical formula $Al(OH)_2C_4H_5N_4O_3$, is similar in effect to allantoin, but the presence of aluminum also adds astringent and bacteriostatic action. It decomposes above about 85°C and below about 100°C and typically below about 95°C.

ALCA, which has the empirical formula $Al_2(OH)_4ClC_4H_5N_4O_3$, has properties similar to ALDA. It is 1.3% soluble in water at 20°C.

Speckled particles formed in accordance with this invention typically comprise about 5 – 10% by weight of allantoin, ALDA or ALCA. Allantoin, ALDA and ALCA may also be present in the base dentifrice. Generally, the total amount of allantoin, ALDA or ALCA or mixtures thereof in the dentifrice is about 0.05 – 1% by weight, preferably about 0.1 – 0.5%.

The binding matrix for speckled particles of allantoin, ALDA or ALCA is a meltable material in which the anti-irritant is easily dispersed when the binder is liquified and with which it is bound when the binder is cooled. The binding matrix should have a melting point lower than the decomposition point of the anti-irritant.

The preferred binding matrix for allantoin, ALDA and ALCA is a glyceryl di- or tri-ester of a $C_{12}$ to $C_{22}$ saturated fatty acid. In addition to glyceryl esters, one may also use the ethylene glycol di-esters. The melting points of these materials are sufficiently low so as to permit use of either allantoin, ALDA or ALCA in the speckles. For instance, grades of glyceryl tristerate melt at about 57°– 6520 C, as well as up to about 72°C.

Other functional additive materials may also be incorporated into the speckles. They may be liquid, which is soluble or insoluble in the binder or solid in finely divided form. The liquids and solids may be colored or colorless as desired. The preferred materials are finely divided solids which may be white or colored, the coloring agent having a particle size less than 2 microns and preferably less than 1 micron. Among suitable solids are the conventional water-insoluble polishing agents which include insoluble phosphate salts, such as insoluble sodium metaphosphate, insoluble potassium metaphosphate, calcium pyrophosphate, magnesium orthophosphate, trimagnesium orthophosphate, tricalcium phosphate, dicalcium phosphate dihydrate, anhydrous dicalcium phosphate and the like. Other polishing agents include calcium carbonate, magnesium carbonate, hydrated alumina, silica, zirconium silicate and aluminum silicate including calcined aluminum silicate. Combinations of polishing agents may also be employed. Water-insoluble coloring matter (e.g. pigments) preservatives, brightening agents, ammoniated materials (e.g., urea, diammonium phosphate) anti-bacterial agents, flavorings and fluorine-containing compounds having a beneficial effect on the oral hygiene of the oral cavity (e.g., sodium and potassium fluoride, stannous fluoride, stannous chlorofluoride, sodium hexafluorostannate, potassium stannous fluoride ($SnF_2·KF$), sodium fluorozirconate and sodium monofluorophosphate) surface active agents, etc. may also be employed.

Generally, the glyceryl ester matrix will comprise the major portion of the speckles, such as from about 50 to 95% by weight of the speckles, although when functional additives in addition to allantoin, ALDA or ALCA are present, the glyceryl ester matrix may be as little as about 1% by weight of the speckles.

In order to obtain the desired speckled effect, it is necessary that the speckles be of macroscopic size (i.e., visible) and generally in the range of about 100 to 1000 microns, preferably 200 to 600 microns and most preferably about 250 to 500 microns. Because of the unique physical and chemical characteristics, i.e., softening point and/or melting point, hardness compatibility, etc. of the glyceryl esters used in this invention, the maximum size of the speckles in the dentifrices is not nearly as critical as that of previously suggested products for this purpose.

The amount of speckles in the oral compositions of this invention may range from 0.01 % to 50% by weight or more preferably from 0.02% to 20% and more preferably 0.05 to 10% by weight of the oral compositions.

The particle size of the solids to be incorporated into and/or with the glyceryl ester must be sufficiently small, generally less than about 200 microns, so as not to feel "gritty" in the mouth. The polishing agents as conventionally used have particle sizes less than about 100 micron and generally less than 75 microns. Other solids, particularly pigments, should have a particle size less than about 2 microns, also; the glyceryl esters used in this invention are generally characterized as soft fatty substances with suitable melting points ranging from about 40°C to 80°C and preferably 55°C to 72°C. Mixtures of esters, conforming to the specifications, are of course, suitable as well.

The speckles of this invention are most conveniently prepared by liquifying the ester and then incorporating additives as desired therewith. The resulting admixture may then be sprayed-cooled to give varying particle sizes depending upon the spray pattern characteristics, pressure of spraying, cooling conditions e.g. temperature of cooling gas, velocity of gas, etc. Suitable conditions merely illustrative, are cooling gas at room temperature, air pressure 2 – 10 atmospheres, etc.

The mixture of ester and additives may also be cooled on a chilled mill roll and recovered in finely divided form in the usual manner. It is preferred to employ spray-cooling since a homogeneous and uniformly sized product can be obtained with the desired particle size more readily controllable.

Suitable coloring agents for the speckles, including white, may be selected from any water-insoluble dye or pigment which are stable in the speckles and do not "bleed" into the main body of the toothpaste. Where the coloring agent is a finely divided solid, it is imperative that the particles have an average particle size of less than 2 microns and preferably less than 1 micron with the maximum particle size not exceeding 5 microns. It is indeed suprising that with such a small particle size there is no bleeding of the colorant into the main body of the toothpaste and one possible explanation for this unique performance is in the fact that the particles are in such a fine state of sub-division and so homogeneously distributed through the ester matrix that only very small quantities, i.e., low concentrations, 0.1 to 2% and preferably 0.2 to 1% are necessary to give an acceptable color density to the speckle. Illustrative materials include titanium dioxide, calcium carbonate, magnesium carbonate, aluminum hydroxide, azulene, coloring agents of the following Color Index numbers: 12490, 75120, 75130, 75810, 69800, 77492, 75470, 75300, 77510, 77007 and 74260 as well as mixtures thereof.

Other binding materials may also be employed, such as resins, gums, gels, waxes, polymers, etc. known in the art as binders. A preferred group of binders in accordance with the invention are natural and synthetic materials classified as thermoplastic, i.e., materials that soften and are rendered moldable when heated. Representative of this latter group are ethylenically unsaturated polymers such as polyethylene, polyvinyl chloride, polyvinyl acetate, copolymers of polyvinyl chloride and vinyl alcohol, vinyl acetate and vinylidene chloride, polystyrene, polymethylstyrene; synthetic rubbers such as styrenebutadiene copolymers and copolymers of alpha methyl styrene and vinyl toluene; polymethacrylates, such as polymethyl methacrylate, polyethyl methacrylate, polyisopropyl methacrylate, polyisobutyl methacrylate; polyacrylates; polyamide, such as nylon; cellulosics such as acetates and butyrates; polycarbonates; phenoxys such as polymers of bisphenol-A and epichlorhydrin; polymers of monomers containing at least 2 polymerizable groups that are initially rendered moldable when heated and subsequently harden when heating is continued, such as polyallyl methacrylate and the polymers of the di-esters of methacrylic acid and ethylene glycol; coumarone-indene resins, polyethylene glycols, and natural waxes such as carnauba and paraffin, and mixtures of the foregoing materials.

In accordance with a specific aspect of the present invention, advantages results can be obtained by utilizing a thermoplastic binding agent having a molecular weight between about 500 and about 20,000 and preferably at least about 1000. The hardness, expressed as tenths of mm needle penetration 100 grams/5 sec/25°C (ASTMD1321) of preferred materials in this class is typically between about 1 and 15 although harder grades can be used if not objectionable in the final toothpaste. The following table lists the properties of thermoplastic binding agents representative of this preferred class.

| Resin | Average Molecular Weight | Softening Point (Approx.) | Hardness | Specific Gravity | Average Viscosity CP |
| --- | --- | --- | --- | --- | --- |
| polyethylene[1] | 2,000 | 105° C | 3.5 | 0.92 | 200 (140° C) |
| polyethylene | 2,200 | 107° C | 3.0 | 0.92 | 220 (140° C) |
| polyethylene | 3,500 | 116° C | 1.0 | 0.93 | 350 (140° C) |
| polyethylene | 5,000 | 109° C | 2.5 | 0.92 | 4000 (140° C) |
| polyethylene | 1,500 | 102° C | 7.5 | 0.91 | 145 (140° C) |
| polyethylene oxidized | 2,000 | 96° C | 9.5 | 0.91 | 230 (140° C) |
| polyethylene[2] oxidized | 1,800 | 104° C | 4.0 | 0.94 | 320 (125° C) |
| polyethylene | 3,000 | 106° C | 3.0 | 0.94 | 1200 (125° C) |
| Polyamide[3] | 6,000 – 9,000 | 110° C | 4 | 0.98 | 2200 (150° C) |
| Polyamide | 6,000 – 9,000 | 95° C | 15 | 0.98 | 1100 (150° C) |

-continued

| Resin | Average Molecular Weight | Softening Point (Approx.) | Hardness | Specific Gravity | Average Viscosity CP |
| --- | --- | --- | --- | --- | --- |
| Polyamide | 6,000 – 9,000 | 110° C | 3 | 0.98 | 3800 (150° C) |
| Alpha methyl Styrene-vinyl toluene copolymer[4] | 1,000 | 100° C | — | — | 3500 (140° C) |

[1]Available from Allied Chemical Company under the trademark A-C polyethylene grades 6, 6A, 7, 7A, 8, 8A, 615, 617, 617A, G-201, and 400.
[2]Available from Eastman Chemical Products, Kingsport, Tenn. under the trademark EPOLENE. These materials are emulsifiable and have both an acid value and saponification number of 9-10. Similar materials are available from Allied Chemical Company under the trademark A-C polyethylene grades 656, 629, 655 and 680.
[3]Produced from ethylene diamine in accordance with U.S. patent number 2,379,413. Available from the Chemical Division of General Mills Co., Kankakee, Ill. under the trademark Versamid grades 930, 940 and 950.
[4]Available from Picco Resin Company, Clairton, Pa., under the trademark Piccotex 100.

In view of the melting or softening points of these types of binding materials, allantoin can be suitably incorporated therein. However, ALDA decomposes at a lower temperature than these binders melt or soften. ALCA is also unsuitable.

The foregoing materials are non-toxic, tasteless and do not attack the material from which the packaging tube for dentifrice is constructed (e.g., aluminum or lined lead).

As pointed out above, the dentifrice may be a powder but preferably a paste which may be opaque, translucent or transparent. Such pastes contain a dental vehicle which forms a gel or creamy mass of consistency which can be desirably extruded from a collapsible tube, such as an aluminum, lead or plastic tube. The vehicle contains liquids and solids.

In general, the liquid portion comprises water, glycerine, sorbitol, propylene glycol, polyethylene glycol 400 or the like including mixtures thereof. It is usually advantageous to use a mixture of both water and a humectant, such as glycerine, sorbitol, propylene glycol or the like. The total liquid content is generally about 20 – 89.5% by weight of the toothpaste. In transparent and translucent toothpastes, the liquid content of the toothpaste may be about 20 – 89.5% by weight while in opaque toothpastes the total liquid content is usually about 20 – 50%.

The solid portion of the vehicle is a gelling agent, such as the natural and synthetic gums and gum-like materials, such as Irish Moss, tragacanth, alkali metal carboxymethylcellulose and hydroxymethyl carboxyethyl cellulose, polyvinyl pyrrolidone, starch, water soluble, hydrophilic colloidal carboxyvinyl polymers such as those sold under the trademark Carbopol 934 and 940, clay available under the trademark Laponite, and silica aerogels. The solid portion of the vehicle is typically present in an amount up to about 10% by weight of the toothpaste and preferably about 0.5 – 5% by weight.

It is noted that reaction easily occurs between aluminum compounds such as ALDA or ALCA and alkali metal (such as sodium) carboxymethylcellulose to form a precipitate of aluminum carboxymethylcellulose. Since this diminishes the amount of the gelling agent in the dentifrice, when ALDA or ALCA is employed, particularly if it is in the base dentifrice, it is preferred to use a gelling agent other than sodium carboxymethylcellulose as the gelling agent. It is preferred that when ALDA or ALCA is present in the base dentifrice, the gelling agent be Irish moss or hydroxyethylcellulose.

In addition to the above, the base dentifrice generally contains water-insoluble invisible polishing agent having a particle size typical of that employed in the prior art, such as less than about 74 microns. Typical dentally acceptable water-insoluble polishing agents include insoluble sodium metaphosphate, calcium carbonate, dicalcium phosphate (dihydrate and anhydrous), dimagnesium phosphate, tricalcium phosphate, trimagnesium phosphate, alumina trihydrate, anhydrous alumina, zirconium silicate, synthetic amorphous sodium aluminosilicate, crystalline silica and colloidal anhydrous silica. The total amount of polishing agent in the dentifrice may be about 10 to 75% by weight preferably about 15% – 50%.

Allantoin, ALDA, or ALCA may be present in the base dentifrice. The total amount of allantoin, ALDA or ALCA or mixture thereof present in the speckles or in the speckles and the base dentifrice is, as set forth above, generally about 0.01 – 5% by weight, preferably about 0.05 – 1%.

The dentifrice base may also contain surface-active agent in addition to any such agent as may be present in the speckles. It is preferred that the total amount of surface-active agent, including such agent as may be in the speckles, be about 0.05% – 5% by weight, preferably about 1 – 3% of the dentifrice.

Various other materials may be incorporated in the oral preparation of this invention. Examples thereof are coloring or whitening agents, preservatives, silicones, chlorophyll compounds, ammoniated materials, such as urea, diammoniumphosphate and mixtures thereof, and other constitutents. Each of these adjuvants may be typically incorporated in the instant toothpastes in amounts up to about 5%. Where coloring is employed, the speckles may be colored with a suitable contrasting color.

Whitening materials which may be used include titanium dioxide in amounts from about 0.01% to about 10%.

The toothpastes may also contain antibacterial agents in amounts of about 0.01 – 5%. Typical examples of such agents are guanidines, biguanides and amines such as:-

$N^1$-(4-chlorobenzyl)-$N^5$-2,4-dichlorobenzl)biguanide;
p-chlorophenyl biguanide;
4-chlorobenzyhydryl biguanide;
4-chlorobenzhydrylguanylurea;

N-3-lauroxypropyl-N⁵-p-chlorobenzylbiguanide;
1,6-di-(p-chlorophenylbiguanido)hexane;
1,6-bis(2-ethylhexylbiguanido)hexane;
1-(lauryldimethylammonium)-8-(p-chlorobenzyldimethylammonium octane dichloride;
5,6-dichloro-2-guanidinobenzimidazole;
N¹-p-chlorophenyl-N⁵-laurylbiguanide;
5-amino-1,3-bis(2-ethylhexyl)-5-methylhexahydropyrimidine;
and their non-toxic acid addition salts.

Suitable flavoring or sweetening sialagogues may be employed in formulating a flavor for the compositions of the present invention. Examples of suitable flavoring constitutents include the flavoring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and saccharine. Suitably, flavor and sweetening agents may together comprise from about 0.01 – 5% or more of the compositions of the instant invention.

The compositions of the present invention suitably may also contain a fluorine-containing compound having a beneficial effect on the care and hygiene of the oral cavity, e.g., diminution of enamel solubility in acid and protection of the teeth against decay. Examples thereof include sodium fluoride, stannous flouride, potassium fluoride ($SnF_2 \cdot KF$), sodium hexalfluorostannate, stannous chlorofluoride, sodium fluorozirconate and sodium monofluorophosphate. These materials, which dissociate or release fluorine-containing ions in water, suitably may be present in an effective but non-toxic amount, usually within the range of about 0.01 to 1% by weight of the water soluble fluorine content thereof.

The most preferred speckles of the present invention are prepared with glyceryl-tristearate and contain about 5 – 10% by weight of allantoin, ALDA or ALCA and about 0.05 – 10% by weight of coloring material. Allantoin is the preferred anti-irritant. ALDA is also highly desirable.

Other highly desirably speckles are prepared with polyethylene having an average molecular weight of about 1,500, an approximate softening point of 102° C, a hardness of 7.5, a specific gravity of 0.91 and an average viscosity of 145 cps; about 5 – 10% by weight of allantoin and about 0.05 – 10% by weight of coloring material. Desirably, about 5 – 10% of precipitated calcium carbonate is also included in the speckle preparations.

Suggested ranges for some of the functional additives which can be used in the speckles are 1 – 80% by weight of polishing agent, preferably 5 – 50%, 0.01 – 50% by weight of fluorine-containing compound, preferably 0.01 – 20%; 0.01 – 50% by weight of preservatives, 0.01 – 50% by weight of antibacterial agents; and 0.01 – 50% by weight of flavors.

The following examples will serve to illustrate the invention without being considered limitative thereof. Amounts, proportions and parts described in the examples are by weight unless otherwise indicated.

EXAMPLE 1

90 parts of glyceryl tristearate are melted at 72° – 75° C in a suitable vessel and 10 parts of allantoin are added and homogeneously mixed. The mixture is then poured over a Mazzoni pilot 3-roll mill through which water is circulating to cool the mixture. The solidified ester having allantoin bound thereto is escaped off the mill, then put into a granulator and then through a vibrating sieve to yield product 297 – 420 microns in size.

EXAMPLE 2

Example 1 is repeated except that ALDA replaces allantoin.

EXAMPLE 3

Example 1 is repeated except that ALCA replaces allantoin.

EXAMPLE 4

Examples 1 – 3 are repeated except that the particles are sieved to yield product of from 420 – 840 microns in size.

EXAMPLE 5

Examples 1 – 4 are repeated except that the following esters replace glyceryl tristearate:-
A. Glyceryl distearate
B. Glyceryl tripalmitate
C. Glyceryl trilaurate
D. Glyceryl tri-docosylate
E. Glycol distearate

EXAMPLE 6

Examples 1 – 5 are repeated except that in each instance the following coloring materials are added to the ester before melting:-
A. 0.5% Pigment Red 5
B. 1.0% Pigment Red 5
C. 2.0% Pigment Red 5
D. 1.0% Azulene
E. 2.5% Azulene
F. 0.3% C.I. 75120
G. 1.0% C.I. 75810
H. 0.1% C.I. 75470
I. 0.4% C.I. 77510
J. 0.5% C.I. 75130
K. 0.3% C.I. 69800
L. 1.0% C.I. 77007
M. 2.0% C.I. 77007
N. 0.4% Pigment Green No. 7 (Color Index 74260)

The pigments used in this Example all have an average particle size of less than 2 microns.

EXAMPLE 7

Example 1 – 6 are again repeated adding to the ester the following:-
A. 2.0% titanium dioxide
B. 5.0% Calcium carbonate
C. 20.0% titanium dioxide
D. 50.0% Calcium carbonate
E. 5.0% Sodium fluoride
F. 5.0% Sodium monofluorophosphate
G. 60.0% Dicalcium phosphate dihydrate average particle size 4.2 microns
H. 5.0% Sodium benzoate
I. 25.0% Zirconium silicate
J. 35.0% Hydrated alumina
K. 60.0% Dicalcium phosphate dihydrate; 1.5% Azulene
L. 50.0% Hydrated alumina; 0.8% Pigment Red 5
M. 40.0% Zirconium silicate; 0.5% Pigment C.I. 75130

EXAMPLE 8

The following transparent formulation is made:-

|  | Parts |
|---|---|
| Glycerine | 24.80 |
| Sodium Carboxymethyl Cellulose | 1.00 |
| Saccharin | 0.11 |
| Sodium benzoate | 0.50 |
| Sorbitol - 70% aq. solution | 44.90 |
| Deionized water | 3.60 |
| Syloid 244 (silica thickener) | 5.00 |
| Sodium aluminum silicate } | |
| P-820 (polishing agent) } | 16.00 |
| Sodium lauryl sulfate | 2.00 |
| Flavor | .90 |

Into the formulation there are separately incorporated the following speckles in the amounts indicated:-
- A. 5% Example 7 (K) - Glyceryl tristearate 250-420 microns
- B. 5% Example 7 (K) - Glyceryl tristearate 420-840 microns
- C. 5% Example 7 (L) - Glyceryl tristearate 250-420 microns
- D. 5% Example 7 (L) - Glyceryl tristearate 420-840 microns
- E. 5% Example 7 (L) - Glyceryl tristearate 250-420 microns
- F. 3% Example 7 (M) - Glyceryl tristearate 250-420 microns

EXAMPLE 9

The following opaque toothpaste is prepared:-

|  | % |
|---|---|
| Glycerine (98% CP) | 6.12 |
| Sodium Carboxymethyl Cellulose 7MF | 1.00 |
| Sodium Benzoate | 0.50 |
| Saccharin | 0.12 |
| Tetrasodium pyrophosphate | 0.30 |
| Sorbitol (70% aq. solution) | 16.00 |
| Deionized water | 24.61 |
| Calcium Carbonate | 8.00 |
| Dicalcium phosphate dihydrate | 40.00 |
| Sodium N-Lauroyl Sarcosinate | 2.05 |
| Titanium dioxide | 0.30 |
| Flavor | 0.80 |
|  | 100.00% |

The following speckles are separately incorporated in the amounts indicated:-
- A - 0.5% 6 (A) - Glyceryl tristearate 240-420 microns
- B - 0.5% 6 (D) - Glyceryl tristearate 250-420 microns
- C - 0.5% 6 (A) - Glyceryl tristearate 250-420 microns
- D - 0.5% 6 (J) - Glyceryl tristearate 420-840 microns
- E - 0.5% 6 (D) - Glyceryl tristearate 420-840 microns
- F - 0.5% 6 (J) - Glyceryl tristearate 420-840 microns
- G - 0.4% 6 (N) - Glyceryl tristearate 296-420 microns

EXAMPLE 10

The following clear gel dentifrice formulation containing sodium aluminosilicate polishing agent is prepared:-

|  | Parts |
|---|---|
| Sorbitol (70% aq. solution) | 44.68 |
| Laponite (synthetic hectorite) | 2.00 |
| Glycerine | 26.10 |
| Deionized water | 3.00 |
| Syloid 244 (thickener) | 5.00 |
| Sodium N-lauryl sarcosinate | 2.00 |
| Saccharin, sodium | 0.17 |
| Sodium aluminum silicate | 16.00 |
| Flavor | 1.00 |

The speckles of Example 9 are also employed in this example.

EXAMPLE 11

Example 9 is repeated except that there is present in the toothpaste 0.5% allantoin in place of an equal amount of water.

EXAMPLE 12

0.5% speckles of Example 6(N) are distributed in 99.5% of the following toothpaste.

|  | % |
|---|---|
| Glycerol | 18 - 24 |
| Hydroxyethylcellulose | 1 - 2 |
| Sodium saccharin | 0.1 - 0.3 |
| Hydrated alumina | 48 - 56 |
| Sodium lauryl sulfate | 1 - 1.5 |
| Pyridyl carbinol | 0.05 - 0.2 |
| Allantoin | 0.1 - 0.2 |
| Methyl parahydroxybenzoate | 0.05 - 0.15 |
| Flavor | 1 |
| Water | Q.S. to 100 |

EXAMPLE 13

Example 12 is repeated except that ALDA replaces allantoin.

EXAMPLE 14

3% of speckled particles prepared in accordance with the following procedure are incorporated into the clear gel dentifrice of Example 8.

90 parts of a non-emulsifiable grade of polyethylene in particulate form having the following properties:

| Molecular weight | approx. 1,500 |
|---|---|
| Softening Point | 102° C |
| Hardness | 7.5 |
| Specific Gravity | 0.91 |
| Viscosity cps. 140° C Brookfield | 145 | are dry mixed with 10 parts of allantoin in a suitable vessel. The vessel containing the dry mix is heated in a suitable heating apparatus and stirred while being heated. When the polyethylene binder softens and before becoming molten, the vessel is removed from the heating apparatus and cooled while still being stirred. The cooled mass is then ground to particulate form and screened to obtain particles 250 - 420 microns in size.

EXAMPLE 15

Example 14 is repeated with the inclusion of 0.4 parts Color Index Pigment Green 7 in the mix.

EXAMPLE 16

The speckles of Example 15 are prepared using 5 parts less of polyethylene and including 5 parts of calcium carbonate. 0.5 parts of the speckles are incorporated into 99.5 parts of the toothpaste of Example 11.

EXAMPLE 17

90 parts of glyceryl tristearate are melted at 72°–75°C in a suitable vessel and 10 parts of allantoin are added and homogeneously mixed and sprayed and cooled at room temperature. The particles thereby formed are sieved to a product size of 292–420 microns. This procedure is repeated using ALDA in place of allantoin. The particles may be colored in accordance with earlier examples and incorporated into toothpastes.

Although the foregoing specific examples include preferred and typical formulations, they should not be taken as limitations on the invention.

I claim:

1. An opaque, transparent of translucent toothpaste dentifrice preparation comprising a toothpaste dentifrice base containing about 10–75% by weight of the preparation of a dentally acceptable water-insoluble polishing agent and about 0.15–50% by weight of the preparation of finely divided visible functional particles, which alleviate periodontal sensitivity and bleeding upon application to teeth and gums, having macroscopic size of 100 to 1000 microns, comprising a matrix of meltable binding material which binding material is a $C_{12}$–$C_{22}$ saturated fatty acid di- or tri-ester of glycercol or ethylene glycol and about 5–10% by weight of anit-irritant compound selected from the group consisting of allantoin, aluminum dihydroxy allantoinate and aluminum chlorohydroxy allantoinate, said meltable binding material having a melting or softening point lower than the decomposition point of said anit-irritant compound, the total amount of said anti-irritant compound being about 0.1–5% by weight of the preparation.

2. The dentifrice preparation as claimed in claim 1, wherein said particles contain a dentally acceptable water-insoluble polishing agent.

3. The dentifrice preparation as claimed in claim 1 wherein said particles are about 250–420 microns in size.

4. The dentifrice preparation as claimed in claim 1 wherein said anti-irritant compound is allantoin.

5. The dentifrice preparation as claimed in claim 2 wherein said polishing agent is present in amount of about 5–10% by weight of said particles and is calcium carbonate and said particles also contain 0.05–10% by weight of pharmaceutically acceptable water-insoluble coloring material.

6. The dentifrice composition claimed in claim 1 wherein the dentifrice base carrying said finely divided particles comprises an anti-irritant compound selected from the group consisting of allantoin, aluminum dihydroxy allantoinate and alluminum chlorohydroxyallantoinate.

7. The dentifrice preparation as claimed in claim 1 wherein said binding material is glyceryl tristearate.

8. The dentifrice preparation as claimed in claim 1 wherein said binding material is glyceryl tristearate.

9. The dentifrice preparation as claimed in claim 1 wherein said binding material is glyceryl tristearate.

* * * * *